United States Patent
Hayashi (10) Patent No.: US 10,362,931 B2
(45) Date of Patent: Jul. 30, 2019

(54) OPTICAL DEVICE (71) Applicant: PANASONIC INTELLECTUAL PROPERTY MANAGEMENT CO., LTD., Osaka (JP)

(72) Inventor: Shintaro Hayashi, Hyogo (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 15/958,033

(22) Filed: Apr. 20, 2018

(65) Prior Publication Data
US 2018/0317757 A1 Nov. 8, 2018

(30) Foreign Application Priority Data
May 2, 2017 (JP) ................. 2017-091848

(51) Int. Cl.
F21V 29/00 (2015.01)
A61B 1/06 (2006.01)
A61B 1/07 (2006.01)
A61B 1/00 (2006.01)
G02B 23/24 (2006.01)
A61B 1/12 (2006.01)

(52) U.S. Cl.
CPC ........ A61B 1/0669 (2013.01); A61B 1/00117 (2013.01); A61B 1/00126 (2013.01); A61B 1/0653 (2013.01); A61B 1/07 (2013.01); G02B 23/2469 (2013.01); A61B 1/128 (2013.01)

(58) Field of Classification Search
None
See application file for complete search history.

(56) References Cited

U.S. PATENT DOCUMENTS

| 2006/0279950 A1* | 12/2006 | Hama ............. A61B 1/0653 362/257 |
|---|---|---|
| 2009/0040598 A1 | 2/2009 | Ito |
| 2013/0331654 A1 | 12/2013 | Hermanowski |
| 2014/0296638 A1 | 10/2014 | Komukai |
| 2017/0035275 A1 | 2/2017 | Yajima et al. |
| 2017/0209032 A1 | 7/2017 | Matsunobu et al. |

FOREIGN PATENT DOCUMENTS

| JP | 2005-236226 | 9/2005 |
| JP | 5019289 | 9/2012 |
| JP | 5649747 | 1/2015 |
| JP | 2015-206912 | 11/2015 |
| JP | 2015-223462 | 12/2015 |
| WO | 2013/094569 | 6/2013 |

OTHER PUBLICATIONS

U.S. Appl. No. 15/977,366 to Kenichiro Tanaka, filed May 11, 2018.

* cited by examiner

Primary Examiner — Vip Patel
(74) Attorney, Agent, or Firm — Greenblum & Bernstein, P.L.C.

(57) ABSTRACT

An optical device is provided. The optical device includes an excitation light source that emits excitation light. A first optical fiber guides the excitation light emitted from the excitation light source. A fluorescent plate includes a fluorescent light emitter that receives the excitation light guided by the first optical fiber and emits fluorescent light. The fluorescent plate further includes a dichroic mirror on a side of the fluorescent light emitter that receives the excitation light. The dichroic mirror transmits the excitation light and reflects the fluorescent light.

16 Claims, 4 Drawing Sheets

OPTICAL DEVICE

CROSS REFERENCE TO RELATED APPLICATION

This application claims the benefit of priority of Japanese Patent Application Number 2017-091848 filed on May 2, 2017, the entire content of which is hereby incorporated by reference.

BACKGROUND

1. Technical Field

The present disclosure relates to an optical device to be used for an endoscope.

2. Description of the Related Art

One of conventionally disclosed optical fiber lighting devices includes: an excitation light source that emits excitation light; a wavelength converter that receives the excitation light and emits wavelength-converted light having a wavelength different from a wavelength of the excitation light; and a first optical fiber that guides the excitation light emitted from the excitation light source (see, for example, Japanese Patent No. 5019289).

SUMMARY

However, this optical fiber lighting device includes, around a light exit surface of the first optical fiber, a reflecting member that reflects light toward a light entrance region of a second optical fiber. The structure of such an optical fiber lighting device is complicated. Moreover, recent demand for a thinner endoscope to reduce the burden of patients makes it difficult to provide an optical fiber lighting device with a simple structure while ensuring output of light emitted from the second optical fiber.

In light of this, it is an object of the present disclosure to provide an optical device which has a simple structure and is capable of ensuring output of emitted light.

In order to achieve the above object, an optical device according to an embodiment of the present disclosure includes: an excitation light source that emits excitation light; a first optical fiber that guides the excitation light emitted from the excitation light source; and a wavelength-conversion plate that includes: a wavelength converter that receives the excitation light guided by the first optical fiber and emits wavelength-converted light; and a reflective film on a side of the wavelength converter that receives the excitation light. The reflective film transmits the excitation light and reflects the wavelength-converted light.

According to the present disclosure, it is possible to provide an optical device which has a simple structure and is capable of ensuring output of emitted light.

BRIEF DESCRIPTION OF DRAWINGS

The figures depict one or more implementations in accordance with the present teaching, by way of examples only, not by way of limitations. In the figures, like reference numerals refer to the same or similar elements.

DETAILED DESCRIPTION OF THE EMBODIMENT

Hereinafter, an embodiment of the present disclosure will be described with reference to the drawings. The embodiment described below shows one specific example of the present disclosure. Therefore, the numerical values, shapes, materials, structural elements, the arrangement and connection of the structural elements, etc., illustrated in the embodiment below are mere examples, and are not intended to limit the present disclosure. As such, among the structural elements in the embodiment below, structural elements not recited in any one of the independent claims defining the most generic concepts of the present disclosure are described as arbitrary structural elements.

Moreover, the term "approximately . . . " is intended to mean, in an example case of "approximately the same", not only exactly the same, but also what would be recognized as essentially the same.

Note that each figure is a schematic illustration and not necessarily a precise illustration. Additionally, throughout the figures, structural elements that are essentially the same share like reference signs, and overlapping descriptions thereof are omitted or simplified.

Hereinafter, an optical device according to Embodiment of the present disclosure will be described.

Embodiment

[Configuration]

Figure 1:
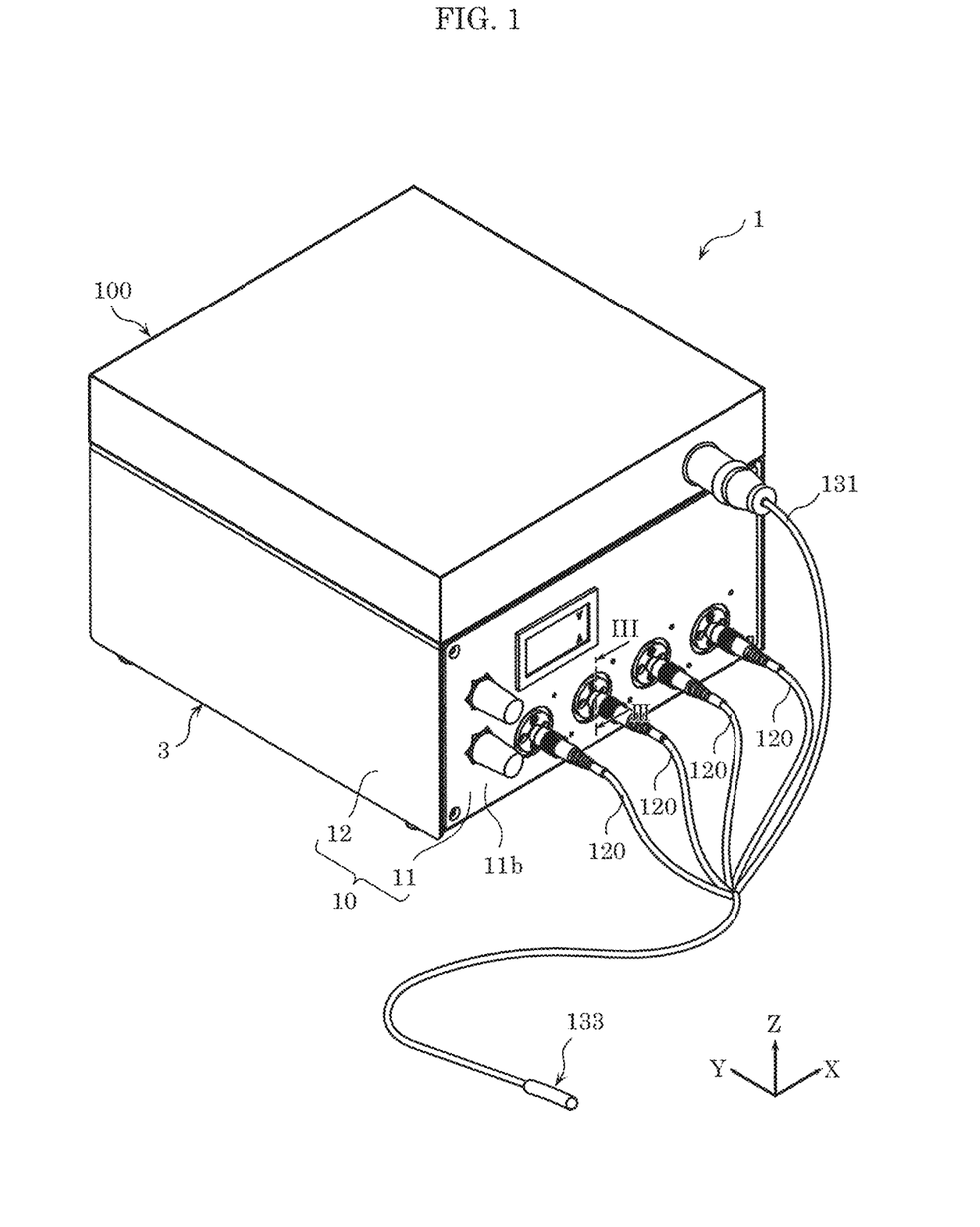
FIG. 1 is a perspective view illustrating an optical device according to Embodiment.
Figure 2:
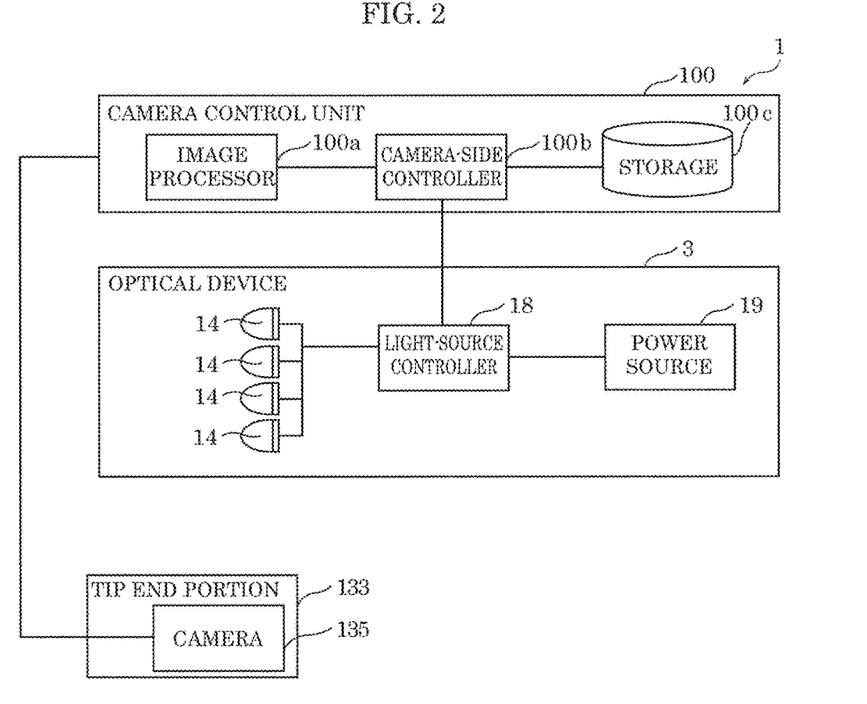
FIG. 2 is a block diagram illustrating an optical device according to Embodiment.
Figure 3:
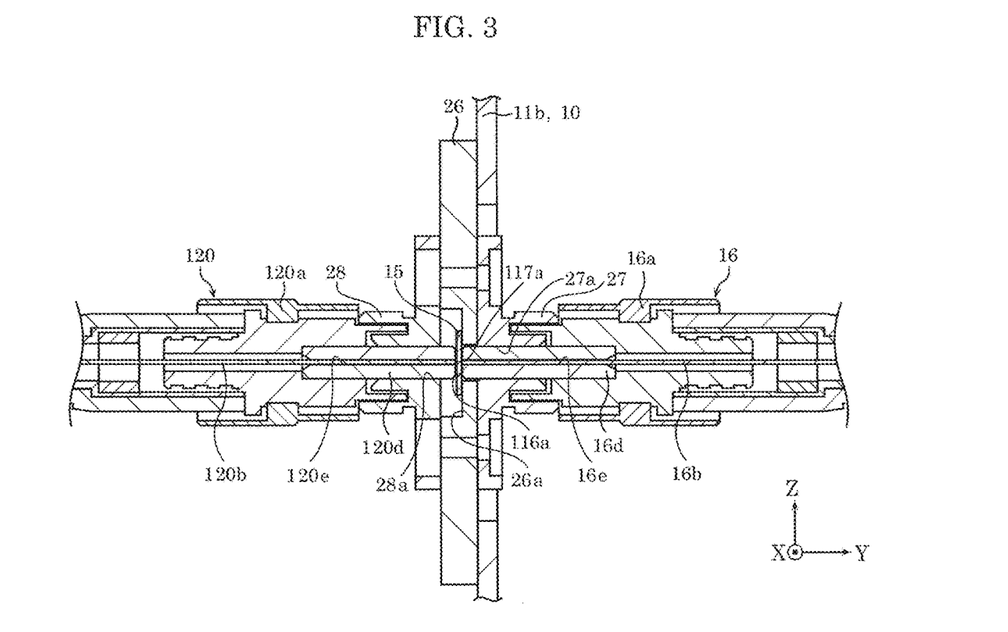
FIG. 3 is a cross sectional view taken along line III-III in FIG. 1, illustrating, for example, a first optical fiber cable, a fluorescent light emitter, and a second optical fiber cable of the optical device according to Embodiment.
Figure 4:
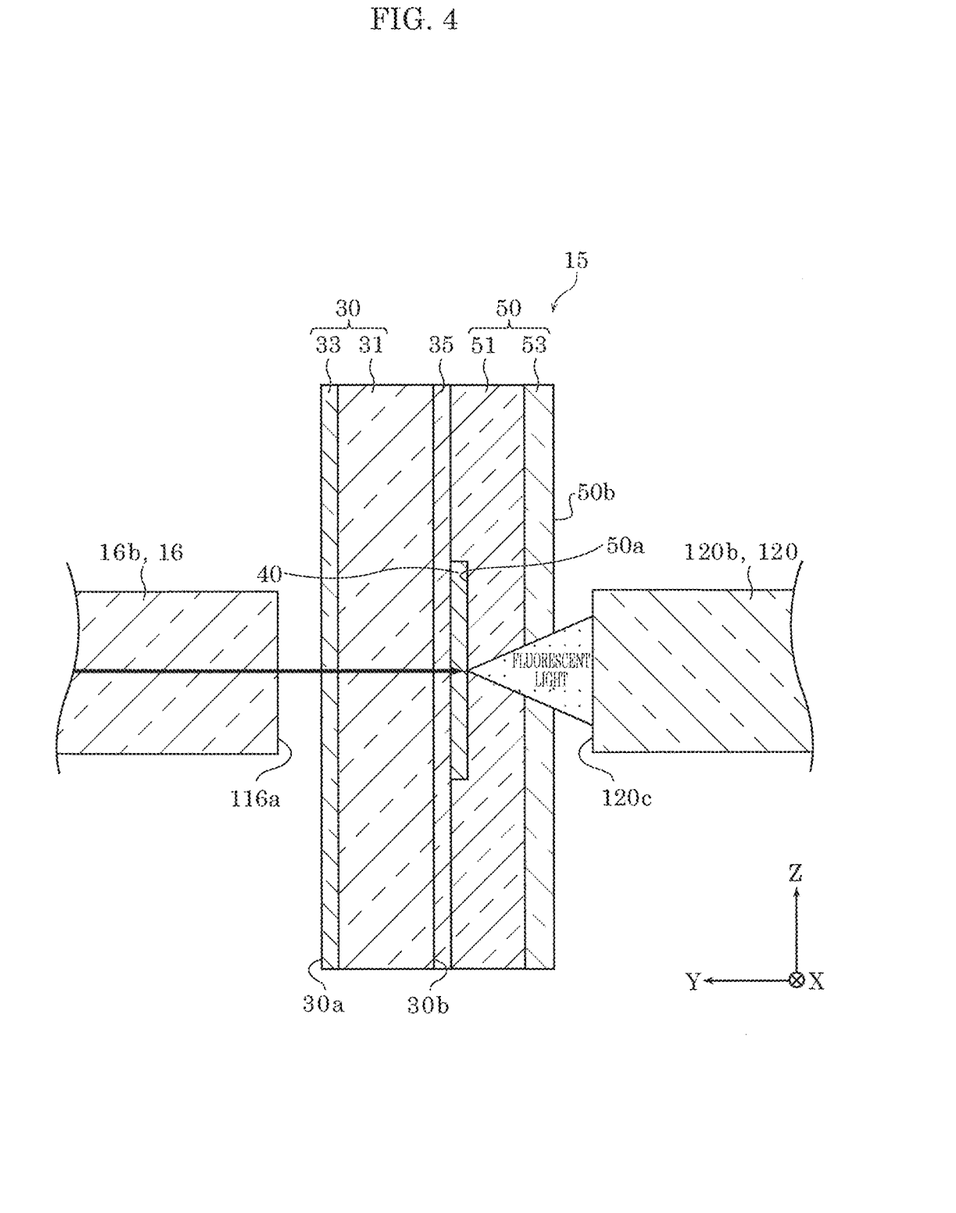
FIG. 4 is a schematic cross-sectional view illustrating, for example, a first transmitter and a second transmitter of the optical device according to Embodiment.

FIG. 1 is a perspective view illustrating optical device 3 according to Embodiment. FIG. 2 is a block diagram illustrating optical device 3 according to Embodiment. FIG. 3 is a cross sectional view taken along line III-III in FIG. 1, illustrating, for example, first optical fiber cable 16, fluorescent light emitter 40, and second optical fiber cable 120 of optical device 3 according to Embodiment. FIG. 4 is a schematic cross-sectional view illustrating, for example, first transmitter 30 and second transmitter 50 of optical device 3 according to Embodiment. In FIG. 4, first end connector 16a, first end connector 120a, first receptacle 27, second receptacle 28, and housing 10, and so on are omitted. Fluorescent light emitter 40 is an example of the wavelength converter.

As illustrated in FIG. 1, endoscope lighting system 1 according to the present embodiment is used for an endoscope and includes optical device 3, camera control unit 100, second optical fiber cable 120, image transmission cable 131, and tip end portion 133.

One end of a cable group is connected to optical device 3 and camera control unit 100. The cable group includes a plurality of second optical fiber cables 120 that guide the excitation light and image transmission cable 131 that transmits a video. The plurality of second optical fiber cables 120 and image transmission cable 131 are tied into a bundle as the cable group. Tip end portion 133 is provided to the other end of the cable group. Portions inserted into a body, such as the cable group and tip end portion 133, are referred to as an endoscope.

As illustrated in FIG. 1 to FIG. 3, optical device 3 includes housing 10, a plurality of excitation light sources 14, a plurality of fluorescent plates 15, a plurality of first optical fiber cables 16, light-source controller 18, and power source 19. The plurality of excitation light sources 14, the plurality of fluorescent plates 15, the plurality of first optical fiber cables 16, light-source controller 18, and power source 19 are housed in hosing 10 of optical device 3. Fluorescent plate 15 is an example of the wavelength-conversion plate.

Housing 10 is a rectangular casing and includes first cover 11 and second cover 12.

First cover 11 is a cover of housing 10 located on the negative side of the Z axis relative to housing 10, and is formed using a metal plate, for example. First cover 11 includes a bottom portion having an approximately rectangular flat shape, first wall portion 11b rising from one edge of the bottom portion, and a second wall portion rising from another edge of the bottom portion and approximately parallel to first wall portion 11b. The plurality of excitation light sources 14, power source 19, a heat sink, a plurality of air blowers, and so on are fixed to the bottom portion.

As illustrated in FIG. 3, first receptacle 27, holding plate 26, and second receptacle 28 are connected to first wall portion 11b.

First receptacle 27 is fixed to first wall portion 11b, and is connected to first optical fiber cable 16. First receptacle 27 is a connection terminal connected to first optical fiber cable 16. Holding plate 26 has a plate shape and includes metal, and has recess 26a that houses fluorescent plate 15.

Holding plate 26 is located on the negative side of the Y axis relative to first wall portion 11b and first receptacle 27, and is fixed to first wall portion 11b and first receptacle 27. Second receptacle 28 is located on the negative side of the Y axis relative to first wall portion 11b, fixed to holding plate 26, and is connected to second optical fiber cable 120. Holding plate 26 is thermally connected to fluorescent plate 15 disposed in recess 26a. In the present embodiment, fluorescent plate 15 is thermally connected to holding plate 26 using silver paste, however, heat-conductive material other than the silver paste may be used. In the present embodiment, the heat generated at fluorescent light emitter 40 of fluorescent plate 15 is dissipated to housing 10 via holding plate 26. Thus, holding plate 26 and housing 10 serve as a heat sink.

Note that housing 10 and holding plate 26 do not necessarily include metal but may include resin which has excellent heat conductivity.

Second receptacle 28 is fixed to holding plate 26 to sandwich holding plate 26 with first receptacle 27. Second receptacle 28 is a connection terminal connected to second optical fiber cable 120. Holding plate 26 is an example of the heat dissipater.

In the present embodiment, four first receptacles 27, four holding plates 26, and four second receptacles 28 are connected to first wall portion 11b. However, the number of each constituent element is not limited to four, and may be equal to or less than three or greater than or equal to five.

As illustrated in FIG. 1, second cover 12 is a cover of housing 10 located on the positive side of the Z axis relative to housing 10, and is formed using a metal plate, for example. Second cover 12 covers first cover 11 from the positive side of the Z axis.

As illustrated in FIG. 1 and FIG. 2, excitation light source 14 is a light source that emits excitation light. Excitation light source 14 allows the excitation light to enter the other end of corresponding first optical fiber cable 16. The excitation light is laser light that excites phosphors of fluorescent plate 15. The excitation light is, for example, light having a wavelength band of from blue excitation light to purple excitation light, and is capable of causing fluorescent plate 15 to emit fluorescent light. In the present embodiment, the excitation light is assumed to have a wavelength of 445 nm, output of 700 mW, and a beam diameter of $\Phi$ 0.2 mm. Fluorescent light is an example of the wavelength-converted light.

Excitation light sources 14 are fixed to the bottom portion of first cover 11 via the heat sink attached to the bottom portion of first cover 11. The heat sink conducts heat generated by excitation light sources 14 to first cover 11. In the present embodiment, the four excitation light sources 14 are disposed on a surface of the heat sink on the positive side of the Z axis. Note that the number of excitation light sources 14 is not limited to four, and may be equal to or less than three or greater than or equal to five.

Output of excitation light from excitation light sources 14 is controlled by light source controller 18. Excitation light sources 14 may be semiconductor lasers that emit excitation light in a range (wavelength band) from ultraviolet laser light, which is shorter in wavelength than blue laser light, to blue laser light, for example. Indium gallium nitride (InGaN) laser diodes or aluminum indium gallium nitride (AlInGaN) laser diodes, for example, can also be used as excitation light sources 14.

In the present embodiment, the output of excitation light is 0.7 (W), the energy conversion efficiency for excitation light is 120 (lm/W), and the combining efficiency of converted pseudo white light is 12%, for example. In this case, the luminous flux at the tips of second optical fiber cables 120 is 10.08 (lm) (=0.7 (W)×120 (lm/W)×12%).

Note that the excitation light emitted by excitation light sources 14 is not limited to laser light, and may be light in any other form (light emitted by an LED, for example) as long as the light is for exciting phosphors.

As illustrated in FIG. 3, fluorescent plate 15 is a flat plate, and is disposed on first wall portion 11b of first cover 11, approximately parallel to the plane defined by the X axis and the Z axis. In other words, fluorescent plate 15 is disposed close to light exit surface 116a of first optical fiber cable 16 such that the excitation light emitted from light exit surface 116a passes through fluorescent plate 15, as well as close to light entrance surface 120c of second optical fiber cable 120 such that the fluorescent light enters light entrance surface 120c. In the present embodiment, fluorescent plate 15 is approximately perpendicular to an optical axis of the excitation light emitted from light exit surface 116a of first optical fiber cable 16. Note that this optical axis is approximately parallel to the Y-axis direction. In the present embodiment, fluorescent plate 15 is in size of 5.7 mm×5.7 mm, and has a thickness of 0.4 mm.

In the present embodiment, fluorescent plate 15 is fixed in recess 26a of holding plate 26 that is bowed inward in the positive direction of the Y axis from a surface of first wall portion 11b on the negative side of the Y axis. In other words, fluorescent plate 15 is disposed between first receptacle 27 and second receptacle 28 which are fixed to first wall portion 11b. In the present embodiment, four fluorescent plates 15 are provided to first cover 11 and they have the same configuration. Thus, description of the other fluorescent plates 15 is omitted.

Fluorescent plate 15 includes first transmitter 30, dichroic mirror 35, fluorescent light emitter 40, and second transmitter 50. Fluorescent plate 15 is a multilayered structure formed by stacking first transmitter 30, dichroic mirror 35, fluorescent light emitter 40, and second transmitter 50, in the stated sequence. Dichroic mirror 35 is an example of the reflective film.

First transmitter 30 is a material that has light transmissivity and a flat plate shape, and is disposed to be approximately perpendicular to the optical axis of the excitation light emitted from light exit surface 116a of first optical fiber cable 16. First transmitter 30 includes first transmitting substrate 31 and anti-reflective (AR) coat 33.

First transmitting substrate 31 is a substrate that has light transmissivity, and includes material such as sapphire. On the surface of first transmitting substrate 31 on the negative side of the Y axis, dichroic mirror 35 is stacked.

Moreover, first transmitter 30 has first light entrance surface 30a and first light exit surface 30b.

First light entrance surface 30a is a surface of first transmitting substrate 31 on the first optical fiber cable 16 side, and is formed of AR coat 33 applied on first transmitting substrate 31 on the first optical fiber cable 16 side. Moreover, first light exit surface 30b is a surface of first transmitter 30 on a side opposite from first light entrance surface 30a and is on the negative side of the Y axis.

Dichroic mirror 35 is a dielectric multilayer film including materials such as functionally graded materials (FMG), silica ($SiO_2$), and titanium oxide ($TiO_2$). Dichroic mirror 35 transmits excitation light, and reflects fluorescent light. For example, dichroic mirror 35 transmits excitation light having a wavelength band of from blue excitation light to purple excitation light, and reflects light having a wavelength band out of from blue excitation light to purple excitation light.

Dichroic mirror 35 is stacked on a surface of fluorescent light emitter 40 that receives the excitation light. Specifically, dichroic mirror 35 is disposed on first light exit surface 30b side of first transmitter 30 and between first transmitter 30 and fluorescent light emitter 40, and between first transmitter 30 and second transmitting substrate 51. In the present embodiment, dichroic mirror 35 is approximately perpendicular to the optical axis of the excitation light emitted from light exit surface 116a of first optical fiber cable 16. Dichroic mirror 35 is an example of the reflective film.

Fluorescent light emitter 40 is disposed in close contact with dichroic mirror 35 and second transmitting substrate 51 such that the optical axis of the excitation light which is from first optical fiber cable 16 and emitted at first light exit surface 30b of first transmitter 30 passes through fluorescent light emitter 40. In the present embodiment, fluorescent light emitter 40 is approximately perpendicular to the optical axis of the excitation light emitted from light exit surface 116a of first optical fiber cable 16.

Fluorescent light emitter 40 emits fluorescent light using the excitation light emitted by first optical fiber 16b. Specifically, each of fluorescent light emitters 40 is a wavelength converter that converts excitation light that has passed through first transmitter 30 and dichroic mirror 35 into predetermined light. Each fluorescent light emitter 40 includes a phosphor that emits fluorescent light using the excitation light. The phosphor is, for example, an yttrium aluminum garnet (YAG) phosphor or a BaMgAl (BAM) phosphor, and can be selected as appropriate according to the type of excitation light emitted by excitation light source 14. In the present embodiment, the phosphor has a grain diameter of approximately 15 μm. In the present embodiment, excitation light received by each of fluorescent light emitters 40 emits white fluorescent light.

Moreover, the phosphor may be, for example, a red phosphor, a green phosphor, or a blue phosphor, and may emit, for example, red, green, or blue fluorescent light using the excitation light. Although fluorescent light emitter 40 is provided on a part of dichroic mirror 35 in the present embodiment, fluorescent light emitter 40 may be provided on the entirety of dichroic mirror 35.

Note that fluorescent light emitter 40 may include a plurality of types of phosphors each absorbs a part of blue excitation light emitted from excitation light source 14 and emits fluorescent light in a range of from green to yellow. In this fluorescent light emitter 40, for example, when blue excitation light from excitation light source 14 is emitted, (i) green to yellow fluorescent light emitted by the phosphors absorbing a part of the blue excitation light and (ii) the blue excitation light that is not absorbed by the phosphors and has transmitted fluorescent light emitter 40 are mixed, and pseudo white illumination light is obtained.

Moreover, fluorescent light emitter 40 is formed by dispersing nanoparticles of predetermined phosphors to a binder which is a transparent material including ceramic, silicone resin, and so on. In other words, the binder is a medium that bonds the phosphors of fluorescent light emitter 40. The binder included in fluorescent light emitter 40 is not limited to those including ceramic and silicone resin, and other transparent materials such as transparent glass may be used.

Second transmitter 50 is provided on second optical fiber cable 120 side of fluorescent light emitter 40 to sandwich fluorescent light emitter 40 with dichroic mirror 35. Second transmitter 50 is a material that has light transmissivity and a flat plate shape, and is disposed to face dichroic mirror 35 via fluorescent light emitter 40. In the present embodiment, second transmitter 50 is approximately perpendicular to the optical axis of the excitation light emitted from light exit surface 116a of first optical fiber cable 16.

Second transmitter 50 includes second transmitting substrate 51 and light-extraction layer 53.

Second transmitting substrate 51 includes a material that has light transmissivity, and an example of such material includes liquid glass containing zinc oxide. Second transmitting substrate 51 is provided on a surface on the positive side of the Y axis relative to dichroic mirror 35 and fluorescent light emitter 40. Second transmitting substrate 51 sandwiches fluorescent light emitter 40 with dichroic mirror 35 to seal the periphery of fluorescent light emitter 40 except for the part with which fluorescent light emitter 40 is facing dichroic mirror 35.

Light-extraction layer 53 is provided on a surface of second transmitting substrate 51 on the negative side of the Y axis. Light-extraction layer 53 is located between second transmitting substrate 51 and second optical fiber cable 120. Light-extraction layer 53 includes a material that has light transmissivity, and an example of such material includes liquid glass, silica dioxide, and FMG silicone resin.

Moreover, second transmitter 50 has second light entrance surface 50a and second light exit surface 50b.

Second light entrance surface 50a is a surface on fluorescent light emitter 40 side of second transmitting substrate 51, and receives the fluorescent light which has transmitted fluorescent light emitter 40. Second light entrance surface 50a is in close contact with a surface of fluorescent light emitter 40 that emits fluorescent light. In other words, there is no space etc. between second transmitter 50 and fluorescent light emitter 40. Second light exit surface 50b is a surface that emits the fluorescent light which has transmitted second transmitter 50, and is a surface on the negative side of the Y axis of light-extraction layer 53 and facing second optical fiber cable 120.

Each of first optical fiber cables 16 guides the excitation light emitted from corresponding excitation light source 14. First optical fiber cable 16 is connected to: first receptacle 27 fixed to a surface of first cover 11 on the positive side of the Y axis; and a connector provided on excitation light source 14 side.

As illustrated in FIG. 3 and FIG. 4, each first optical fiber cable 16 includes first end connector 16*a*, first optical fiber 16*b*, and second end connector.

First end connector 16*a* is a connection terminal disposed on a first end side of first optical fiber cable 16. First end connector 16*a* includes first position alignment part 16*d* that holds an end portion of first optical fiber 16*b* as a central axis.

First position alignment part 16*d* is a ferrule including, for example, zirconia, nickel, and so on. First position alignment part 16*d* includes first insertion hole 16*e* into which an end portion of first optical fiber 16*b*, that is on the side opposite from excitation light source 14, is inserted. The end portion of first optical fiber 16*b* to be inserted into first insertion hole 16*e* is the end portion of first optical fiber 16*b* on fluorescent plate 15 side. Moreover, when first end connector 16*a* is connected to first receptacle 27, first position alignment part 16*d* is inserted into insertion hole 27*a* of first receptacle 27 and is held by first receptacle 27 such that the tip end of first position alignment part 16*d* is positioned close to fluorescent plate 15.

First optical fiber 16*b* is held such that a space between light exit surface 116*a* of first optical fiber 16*b* and fluorescent light emitter 40 is equal to or less than 0.1 mm. In the present embodiment, light exit surface 116*a* is a surface of first optical fiber 16*b* on the first end side, and is spaced apart from first light entrance surface 30*a* of first transmitter 30. Light exit surface 116*a* faces with first light entrance surface 30*a* approximately parallel to first light entrance surface 30*a*. Note that first optical fiber 16*b* may be in close contact with fluorescent plate 15.

First optical fiber 16*b* is a light-transmissive optical fiber including a material such as quartz glass or plastic, for example. Each of first optical fibers 16*b* guides the excitation light emitted from corresponding excitation light source 14. Specifically, first optical fiber 16*b* receives the excitation light emitted from excitation light source 14 at the second end connector, and emits, from first end connector 16*a*, the excitation light that has been guided inside first optical fiber 16*b* from light exit surface 116*a*. Moreover, first optical fiber 16*b* is covered with coating material including resin and so on. In the present embodiment, first optical fiber 16*b* is quartz fiber that has a core diameter of 0.105 mm and numerical aperture (NA) of 0.22.

Second end connector is a connection terminal disposed on a second end side of first optical fiber cable 16 opposite first end connector 16*a*. Second end connector is connected to a connector of excitation light source 14 to receive the excitation light emitted by excitation light source 14.

Each of second optical fiber cables 120 guides the fluorescent light emitted by corresponding fluorescent light emitter 40. Second optical fiber cable 120 is connected to: second receptacle 28 fixed to a surface of first cover 11 on the negative side of the Y axis; and tip end portion 133.

Each second optical fiber cable 120 includes first end connector 120*a* and second optical fiber 120*b*.

First end connector 120*a* is a connection terminal disposed on a first end side of second optical fiber cable 120.

First end connector 120*a* includes second position alignment part 120*d* that holds an end portion of second optical fiber 120*b* as a central axis.

Second position alignment part 120*d* is a ferrule including, for example, zirconia, nickel, and so on. Second position alignment part 120*d* includes second insertion hole 120*e* into which an end portion of second optical fiber 120*b* that receives the fluorescent light emitted from fluorescent light emitter 40 is inserted. The end portion of second optical fiber 120*b* to be inserted into second insertion hole 120*e* is the end portion of second optical fiber 120*b* on fluorescent plate 15 side. Moreover, when first end connector 120*a* is connected to second receptacle 28, second position alignment part 120*d* is inserted into insertion hole 28*a* of second receptacle 28 and is held by second receptacle 28 such that the tip end of second position alignment part 120*d* is positioned close to fluorescent plate 15. Thus, first position alignment part 16*d* and second position alignment part 120*d* dispose first optical fiber 16*b* and second optical fiber 120*b* to face each other via fluorescent plate 15. Note that an optical axis of the excitation light emitted from first optical fiber 16*b* and an optical axis of the excitation light emitted from second optical fiber 120*b* may be approximately the same. The optical axis of the excitation light entering second optical fiber 120*b* is approximately parallel to the Y-axis direction.

Second optical fiber 120*b* is held such that a space between light entrance surface 120*c* of second optical fiber 120*b* and fluorescent light emitter 40 is equal to or less than 0.1 mm. In the present embodiment, light entrance surface 120*c* is a surface of second optical fiber 120*b* on the first end side, and the fluorescent light and the excitation light emitted from second light exit surface 50*b* are received by light entrance surface 120*c* which is spaced apart from second light exit surface 50*b* of second transmitter 50. In other words, light entrance surface 120*c* is provided to be approximately perpendicular to the optical axis of light emitted from excitation light source 14. The fluorescent light and the excitation light received at light entrance surface 120*c* are guided inside second optical fiber 120*b* and emitted from tip end portion 133 opposite first end connector 120*a*. Note that second optical fiber 120*b* may be in close contact with fluorescent plate 15.

Second optical fiber 120*b* is a light-transmissive optical fiber including a material such as quartz glass or plastic, for example. The light emitted from second transmitter 50 is received at light entrance surface 120*c* of second optical fiber 120*b*. In the present embodiment, second optical fiber 120*b* is multicomponent glass fiber that has a core diameter of 0.12 mm and NA of 0.87.

In the present embodiment, light entrance surface 120*c* of second optical fiber cable 120 seen in the Y-axis direction overlaps with second light entrance surface 50*a*, second light exit surface 50*b*, fluorescent light emitter 40, first light exit surface 30*b*, first light entrance surface 30*a*, and light exit surface 116*a* of first optical fiber cable 16. Note that sizes of light entrance surface 120*c* of second optical fiber cable 120, second light entrance surface 50*a*, second light exit surface 50*b*, fluorescent light emitter 40, first light exit surface 30*b*, first light entrance surface 30*a*, and light exit surface 116*a* of first optical fiber cable 16 may be changeable as appropriate.

In the present embodiment, there are four excitation light sources 14, four first receptacles 27, and four second receptacles 28 having the same configurations are provided, and thus, description of the other first optical fiber cables 16 and the other second optical fiber cables 120 is omitted.

Light-source controller 18 controls operations such as light emission of excitation light sources 14 via power source 19, and includes a circuit and so on for controlling excitation light sources 14. Light-source controller 18 achieves such operations using, for example, a microcomputer, a processor, or a dedicated circuit that controls current supplied to excitation light sources 14, etc.

Power source 19 includes a power source circuit that generates power for causing excitation light sources 14 to emit light. Power source 19 is electrically connected to a power system by a power line such as a control line, for example.

Camera control unit 100 processes an image captured by tip end portion 133. Camera control unit 100 houses, for example, image processor 100a, camera-side controller 100b, and storage 100c.

Second end portions of second optical fiber cables 120 and a second end portion of image transmission cable are connected to tip end portion 133. Tip end portion 133 includes camera 135 that captures an image of an object.

Camera 135 is a charge-coupled device (CCD) camera, for example Camera 135 transmits a signal of the captured image of the object to image processor 100a of camera control unit 100 via image transmission cable. Image processor 100a performs appropriate image processing by converting the input signal of the image into image data, so as to generate output image information desired. The image information generated is then displayed on a display via camera-side controller 100b as an observation image of the endoscope. Moreover, as necessary, camera-side controller 100b stores the image information in storage 100c that includes memory, for example.

With such optical device 3 as described above, the excitation light emitted from each of excitation light sources 14 is: received by and guided inside first optical fiber cable 16; emitted from light exit surface 116a of first optical fiber cable 16; and emitted to first light entrance surface 30a of first transmitter 30. The excitation light received by first light entrance surface 30a is transmitted inside first transmitter 30, emitted from first light exit surface 30b, and received by dichroic mirror 35. The excitation light is transmitted by dichroic mirror 35 and received by fluorescent light emitter 40. Part of the excitation light received by fluorescent light emitter 40 is absorbed by the phosphors and emits fluorescent light, while the rest transmits fluorescent light emitter 40 as it is. Part of the fluorescent light and the excitation light emitted from fluorescent light emitter 40 is received by second light entrance surface 50a, is transmitted by second transmitter 50, emitted from second light exit surface 50b, and received by light entrance surface 120c of second optical fiber cable 120. Moreover, part of the fluorescent light emitted from fluorescent light emitter 40 is reflected by dichroic mirror 35 and travels toward light entrance surface 120c of second optical fiber cable 120. In addition, part of the excitation light emitted from fluorescent light emitter 40 transmits dichroic mirror 35. Then, the fluorescent light and the excitation light are guided through second optical fiber cable 120 toward tip end portion 133 and are emitted from tip end portion 133.

[Experimental Result]

Figure 5:
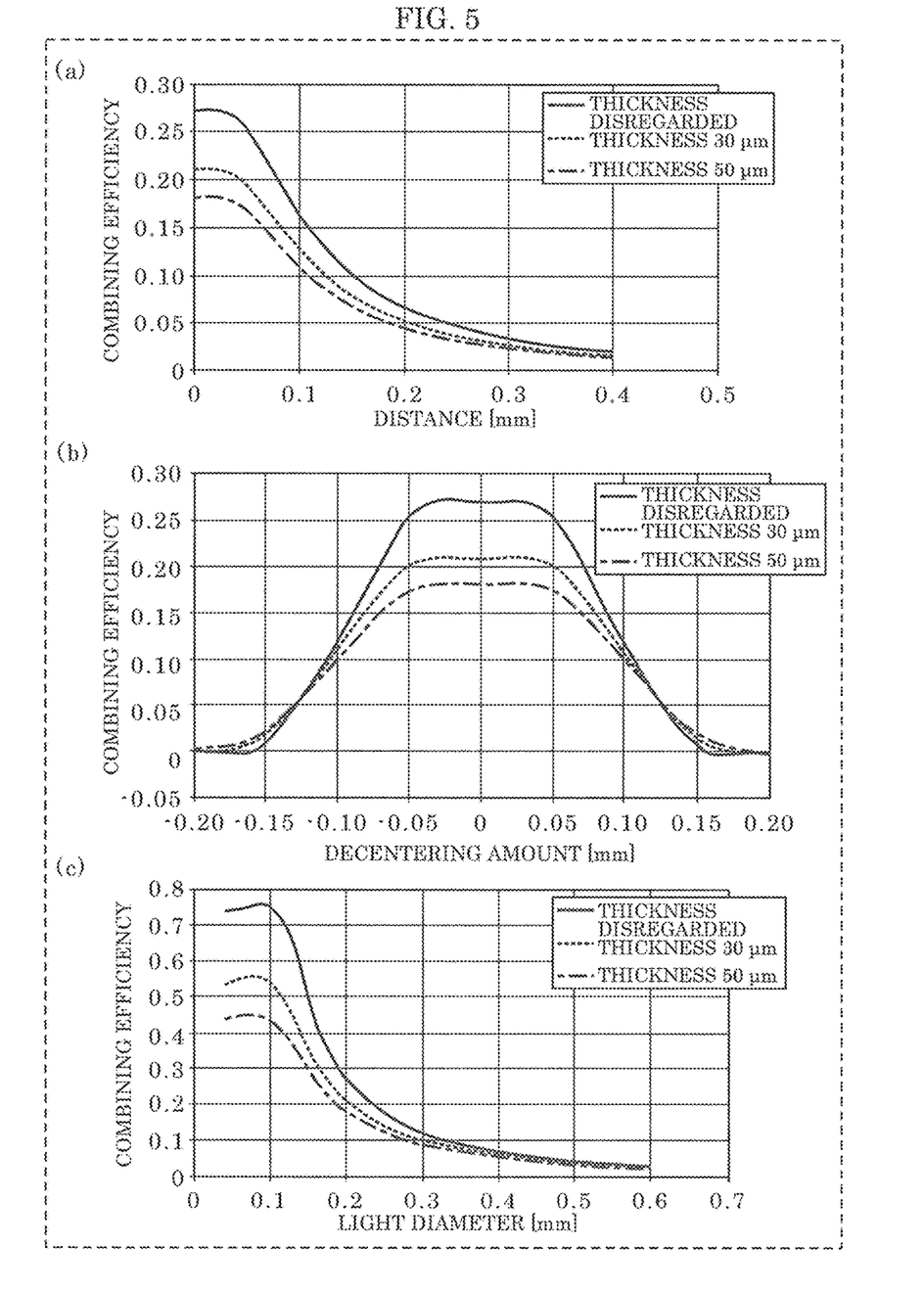
FIG. 5 is a graph indicating combining efficiency of the optical device according to Embodiment.

Next, description will be provided on combining efficiency of optical device 3. FIG. 5 is a graph indicating the combining efficiency of optical device 3 according to the Embodiment.

(a) in FIG. 5 indicates a relationship between the combining efficiency and the distance from fluorescent light emitter 40 to second optical fiber cable 120. In (a) in FIG. 5, NA of second optical fiber cable 120 is assumed to be 0.87 and a light diameter of the excitation light to be emitted to fluorescent light emitter 40 is assumed to be 0.2 mm. The solid line indicates the case where the thickness of fluorescent light emitter 40 is disregarded, the broken line indicates the case where the thickness of fluorescent light emitter 40 is assumed to be 30 µm, and the dashed-dotted line indicates the case where the thickness of fluorescent light emitter 40 is assumed to be 50 µm. Here, the light diameter of fluorescent light emitted from fluorescent light emitter 40 is approximately the same as a diameter of the excitation light emitted from light exit surface 116a of first optical fiber cable 16 when being emitted to fluorescent light emitter 40, and is also approximately the same as a diameter of the fluorescent light emitted by fluorescent light emitter 40.

As it is understood from the graph in (a) in FIG. 5, the combining efficiency increases as the distance between fluorescent light emitter 40 and second optical fiber cable 120 decreases. Moreover, it is understood that the combining efficiency increases as the thickness of fluorescent light emitter 40 decreases. It is understood that the distance may be particularly equal to or less than 0.05 mm.

(b) in FIG. 5 shows a relationship between the combining efficiency and decentering amount. In (b) in FIG. 5, NA of second optical fiber cable 120 is assumed to be 0.87, the light diameter is assumed to be 0.2 mm, and the distance between fluorescent light emitter 40 and second optical fiber cable 120 is assumed to be 0.1 mm. The solid line indicates the case where the thickness of fluorescent light emitter 40 is disregarded, the broken line indicates the case where the thickness of fluorescent light emitter 40 is assumed to be 30 µm, and the dashed-dotted line indicates the case where the thickness of fluorescent light emitter 40 is assumed to be 50 µm. The decentering amount is an amount of deviation of the central axis of second optical fiber 120b with respect to the optical axis of the fluorescent light emitted from fluorescent light emitter 40.

As it is understood from the graph in (b) in FIG. 5, the combining efficiency increases as the decentering amount gets closer to 0. Moreover, it is understood that the combining efficiency increases as the thickness of fluorescent light emitter 40 decreases. Based on the result, when the decentering amount is equal to or less than 0.1 mm, it is possible to obtain the combining efficiency desired. It is understood that the distance may be particularly equal to or less than ±0.05 mm.

(c) in FIG. 5 shows a relationship between the combining efficiency and the light diameter. In (c) in FIG. 5, NA of second optical fiber cable 120 is assumed to be 0.87, the light diameter is assumed to be 0.2 mm, and the distance between fluorescent light emitter 40 and second optical fiber cable 120 is assumed to be 0.1 mm. The solid line indicates the case where the thickness of fluorescent light emitter 40 is disregarded, the broken line indicates the case where the thickness of fluorescent light emitter 40 is assumed to be 30 µm, and the dashed-dotted line indicates the case where the thickness of fluorescent light emitter 40 is assumed to be 50 µm.

As it is understood from the graph in (c) in FIG. 5, the combining efficiency increases as the light diameter decreases. Moreover, it is understood that the combining efficiency increases as the thickness of fluorescent light emitter 40 decreases. Based on the result, when the light diameter is equal to or less than 0.1 mm, it is possible to obtain the combining efficiency desired. It is understood that the light diameter may be particularly equal to or less than 0.05 mm.

[Effects]

Next, description will be provided on three effects of optical device 3 according to the present embodiment.

As described above, optical device 3 according to the present embodiment includes: excitation light source 14 that emits excitation light; first optical fiber 16b that guides the excitation light emitted from excitation light source 14; and fluorescent plate 15 that includes: fluorescent light emitter 40 that receives the excitation light guided by first optical fiber 16b and emits fluorescent light; and dichroic mirror 35 on a side of fluorescent light emitter 40 that receives the excitation light. In addition, dichroic mirror 35 transmits the excitation light and reflects the fluorescent light.

With this, the excitation light emitted from excitation light source 14 is emitted by first optical fiber 16b to first transmitter 30, and received by fluorescent light emitter 40 via first transmitter 30 and dichroic mirror 35. Moreover, dichroic mirror 35 is provided on a surface of first transmitter 30 opposite the side that receives the excitation light, and between fluorescent light emitter 40 and first transmitter 30. Dichroic mirror 35 transmits the excitation light and reflects the fluorescent light. Therefore, even when part of the fluorescent light emitted by fluorescent light emitter 40 travels toward dichroic mirror 35 side, dichroic mirror 35 reflects the fluorescent light, which allows more fluorescent light to be condensed to second optical fiber 120b.

Accordingly, with this optical device 3, it is possible to ensure output of emitted light with a simple structure.

Particularly, this optical device 3 allows, for example, locating first optical fiber 16b closer to fluorescent light emitter 40 as compared with the case where a lens is used for condensing the excitation light emitted from first optical fiber 16b. Therefore, the light diameter of the excitation light emitted by first optical fiber 16b does not increase easily. Moreover, since dichroic mirror 35 is a thin film, light exit surface 116a of first optical fiber 16b and light entrance surface 120c of second optical fiber 120b do not easily go far away from each other. In other words, since the diameter of the excitation light emitted by fluorescent light emitter 40 does not increase easily, it is possible to suppress the increase of the diameter of second optical fiber 120b according to the size of the diameter of the fluorescent light.

Moreover, since this optical device 3 does not include a lens for condensing light, for example, even when the excitation light and the fluorescent light are emitted from second light exit surface 50b while second optical fiber cable 120 is detached, high level of security is ensured.

Moreover, optical device 3 according to the present embodiment further includes: first position alignment part 16d that includes first insertion hole 16e into which an end portion of first optical fiber 16b is inserted, the end portion being opposite from excitation light source 14; and second position alignment part 120d that includes second insertion hole 120e into which an end portion of second optical fiber 120b is inserted, second optical fiber 120b receiving the fluorescent light emitted from fluorescent light emitter 40. In addition, first position alignment part 16d and second position alignment part 120d dispose first optical fiber 16b and second optical fiber 120b to face each other via fluorescent plate 15.

With this, the end portion of first optical fiber 16b on fluorescent light emitter 40 side is inserted into first insertion hole 16e of first position alignment part 16d, which allows the end portion of first optical fiber 16b to be held by first position alignment part 16d. Moreover, the end portion of second optical fiber 120b on fluorescent light emitter 40 side is inserted into second insertion hole 120e of second position alignment part 120d, which allows the end portion of second optical fiber 120b to be held by second position alignment part 120d. First position alignment part 16d and second position alignment part 120d dispose first optical fiber 16b and second optical fiber 120b to face each other via fluorescent plate 15. This allows both light exit surface 116a of first optical fiber 16b and light entrance surface 120c of second optical fiber 120b to be held close to fluorescent light emitter 40. Therefore, the optical axis of the excitation light emitted from first optical fiber 16b and the optical axis of the fluorescent light received by second optical fiber 120b can be approximately the same. As a result, this optical device 3 makes it possible to ensure output of light emitted from second optical fiber 120b more certainly.

Moreover, in optical device 3 according to the present embodiment, a space between second optical fiber 120b and fluorescent light emitter 40 is equal to or less than 0.1 mm.

With this structure, it is possible to improve incidence efficiency of the fluorescent light received by light entrance surface 120c of second optical fiber 120b without increasing the diameter of second optical fiber 120b. Therefore, it possible to ensure output of light emitted from second optical fiber 120b more certainly.

Moreover, in optical device 3 according to the present embodiment, a space between first optical fiber 16b and fluorescent light emitter 40 is equal to or less than 0.1 mm.

With this structure, the spot of the excitation light emitted to fluorescent light emitter 40 does not easily increase. Therefore, it is possible to improve the incidence efficiency of the fluorescent light received by light entrance surface 120c of second optical fiber 120b without increasing the diameter of second optical fiber 120b. Therefore, it is possible to ensure output of the light emitted from second optical fiber 120b more certainly.

Moreover, optical device 3 according to the present embodiment further includes: holding plate 26 thermally connected to fluorescent plate 15.

With this, fluorescent plate 15 is thermally connected to holding plate 26 that also serves as a heat sink, and furthermore, holding plate 26 is thermally connected to housing 10, which enhances the heat dissipation of fluorescent plate 15. Therefore, it is possible to improve the luminous efficiency of the phosphors and ensure output of light emitted from second optical fiber 120b more certainly.

Moreover, in optical device 3 according to the present embodiment, the reflective film is a dichroic mirror.

With this structure, fluorescent plate 15 with a widely used dichroic mirror 35 can be realized.

Moreover, in optical device 3 according to the present embodiment, fluorescent plate 15 further includes: first transmitter 30 that receives the excitation light guided by first optical fiber 16; and second transmitter 50 that transmits the wavelength-converted light emitted from fluorescent light emitter 40. In addition, dichroic mirror 35 is between first transmitter 30 and fluorescent light emitter 40, and between first transmitter 30 and second transmitter 50.

Moreover, in optical device 3 according to the present embodiment, the excitation light has a wavelength band of from blue excitation light to purple excitation light.

Moreover, optical device 3 according to the present embodiment further includes: first ferrule 16d that includes first insertion hole 16e into which an end portion of first optical fiber 16 is inserted; and second ferrule 120d that includes second insertion hole 120e into which an end portion of second optical fiber 120 is inserted. The end portion of first optical fiber 16 is opposite from excitation light source 14, and second optical fiber 120 receives the wavelength-converted light emitted from fluorescent light emitter 40. Furthermore, in optical device 3, first ferrule 16d and second ferrule 120d dispose first optical fiber 16 to face second optical fiber 120 via fluorescent plate 15. First position alignment part 16d is an example of the first ferrule. Second position alignment part 120d is an example of the second ferrule.

Moreover, in optical device 3 according to the present embodiment, fluorescent plate 15 further includes: a first substrate that receives the excitation light guided by first optical fiber 16; and a second substrate that transmits the wavelength-converted light emitted from fluorescent light emitter 40. Furthermore, dichroic mirror 35 is between the first substrate and fluorescent light emitter 40, and between the first substrate and the second substrate. First transmitter 30 is an example of the first substrate. Second transmitter 50 is an example of the second substrate.

Moreover, optical device 3 according to the present embodiment includes: excitation light source 14 that emits excitation light; first optical fiber 16 that guides and emits the excitation light emitted from excitation light source 14; fluorescent plate 15 that includes: fluorescent light emitter 40 that receives the excitation light guided and emitted from first optical fiber 16, wavelength-converts the excitation light received, and emits wavelength-converted light; and dichroic mirror 35 on a side of fluorescent light emitter 40 that receives the excitation light. In addition, dichroic mirror 35 transmits the excitation light and reflects the wavelength-converted light.

OTHER VARIATIONS ETC.

The present disclosure has been described based on the Embodiment, but the present disclosure is not limited to the Embodiment.

For example, in the above embodiment, the phosphors may include various kinds of phosphors including, for example, powder phosphors, ceramic phosphors, and single-crystal phosphors.

Moreover, although the optical device is used for an endoscope in the above embodiment, it may also be used for a projector.

Various modifications to Embodiment and the variation of Embodiment conceived by those skilled in the art, as well as embodiments resulting from combinations of structural elements of different embodiments may be included within the scope of one or more aspects of the present disclosure, as long as such modifications and embodiments do not depart from the essence of the present disclosure.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. An optical device, comprising:
   an excitation light source that emits excitation light;
   a first optical fiber that guides the excitation light emitted from the excitation light source; and
   a wavelength-conversion plate that includes: a wavelength converter that receives the excitation light guided by the first optical fiber and emits wavelength-converted light; and a reflective film on a side of the wavelength converter that receives the excitation light,
   wherein the reflective film is spaced from a light exit surface of the first optical fiber, transmits the excitation light, and reflects the wavelength-converted light.

2. The optical device according to claim 1, further comprising:
   a first position alignment part that includes a first insertion hole into which an end portion of the first optical fiber is inserted, the end portion of the first optical fiber being opposite from the excitation light source; and
   a second position alignment part that includes a second insertion hole into which an end portion of a second optical fiber is inserted, the second optical fiber receiving the wavelength-converted light emitted from the wavelength converter,
   wherein the first position alignment part and the second position alignment part dispose the first optical fiber to face the second optical fiber via the wavelength-conversion plate.

3. The optical device according to claim 2,
   wherein a space between the second optical fiber and the wavelength converter is equal to or less than 0.1 mm.

4. The optical device according to claim 2,
   wherein a space between the first optical fiber and the wavelength converter is equal to or less than 0.1 mm.

5. The optical device according to claim 1, further comprising:
   a heat dissipater thermally connected to the wavelength-conversion plate.

6. The optical device according to claim 1,
   wherein the reflective film is a dichroic mirror.

7. The optical device according to claim 1,
   wherein the wavelength-conversion plate further includes: a first transmitter that receives the excitation light guided by the first optical fiber; and a second transmitter that transmits the wavelength-converted light emitted from the wavelength converter, and
   the reflective film is between the first transmitter and the wavelength converter, and between the first transmitter and the second transmitter.

8. The optical device according to claim 1,
   wherein the excitation light has a wavelength band from blue excitation light to purple excitation light.

9. The optical device according to claim 1, further comprising:
   a first ferrule that includes a first insertion hole into which an end portion of the first optical fiber is inserted, the end portion of the first optical fiber being opposite from the excitation light source; and
   a second ferrule that includes a second insertion hole into which an end portion of a second optical fiber is inserted, the second optical fiber receiving the wavelength-converted light emitted from the wavelength converter,
   wherein the first ferrule and the second ferrule dispose the first optical fiber to face the second optical fiber via the wavelength-conversion plate.

10. The optical device according to claim 1,
    wherein the wavelength-conversion plate further includes: a first substrate that receives the excitation light guided by the first optical fiber; and a second substrate that transmits the wavelength-converted light emitted from the wavelength converter, and
    the reflective film is between the first substrate and the wavelength converter, and between the first substrate and the second substrate.

11. The optical device according to claim 1,
wherein the reflective film is stacked on the wavelength converter to cover a surface on the side of the wavelength converter that receives the excitation light.

12. The optical device according to claim 1,
wherein the reflective film is transverse to an optical axis of the excitation light, between the light exit surface of the first optical fiber and the wavelength converter, with the wavelength converter converting the excitation light that passes through the reflective film.

13. The optical device according to claim 1,
wherein the reflective film is perpendicular to the optical axis of the excitation light, between the light exit surface of the first optical fiber and the wavelength converter, with the wavelength converter converting the excitation light that passes through the reflective film.

14. The optical device according to claim 13,
wherein the wavelength converter is on an entirety of the reflective film.

15. The optical device according to claim 13,
wherein the reflective film transmits light having a wavelength band of blue light to purple light, and reflects light outside the wavelength band of blue light to purple light.

16. An optical device, comprising:
an excitation light source that emits excitation light;
a first optical fiber that guides and emits the excitation light emitted from the excitation light source;
a wavelength-conversion plate that includes: a wavelength converter that receives the excitation light guided and emitted from the first optical fiber, wavelength-converts the excitation light received, and emits wavelength-converted light; and a reflective film on a side of the wavelength converter that receives the excitation light,
wherein the reflective film is spaced from a light exit surface of the first optical fiber, transmits the excitation light and reflects the wavelength-converted light.

* * * * *